US009372960B2

(12) United States Patent
Shie et al.

(10) Patent No.: US 9,372,960 B2
(45) Date of Patent: Jun. 21, 2016

(54) MEDICAL SUPPORT SYSTEM AND METHOD THEREOF (71) Applicant: ViewSend ICT Co., Ltd., Tokyo (JP)

(72) Inventors: Kenei Shie, Tokyo (JP); Katsuhiro Ogiwara, Tokyo (JP); Takayuki Kohri, Gunma (JP); Tomio Sasaki, Tokyo (JP); Yuji Nakajima, Tokyo (JP); Guoliang Wang, Tokyo (JP)

(73) Assignee: VIEWSEND ICT CO., LTD., Toshima-Ku, Tokyo (JP)

( * ) Notice: Subject to any disclaimer, the term of this patent is extended or adjusted under 35 U.S.C. 154(b) by 0 days.

(21) Appl. No.: 14/648,991

(22) PCT Filed: Dec. 11, 2012

(86) PCT No.: PCT/JP2012/007898
§ 371 (c)(1),
(2) Date: Jun. 2, 2015

(87) PCT Pub. No.: WO2014/091519
PCT Pub. Date: Jun. 19, 2014

(65) Prior Publication Data
US 2015/0324536 A1    Nov. 12, 2015

(51) Int. Cl.
*G06F 15/16*    (2006.01)
*G06F 19/00*    (2011.01)
(Continued)

(52) U.S. Cl.
CPC .......... *G06F 19/3418* (2013.01); *G06F 3/0482* (2013.01); *G06F 3/04842* (2013.01); *G06F 17/30268* (2013.01); *G06F 19/321* (2013.01); *G06F 19/3425* (2013.01); *G06Q 50/24* (2013.01); *H04L 65/403* (2013.01)

(58) Field of Classification Search
CPC .............. H04L 29/08558; H04L 67/12; H04L 2209/88; H04L 29/06176; H04L 29/06414; H04L 41/50; H04L 65/403
USPC .......................... 709/204, 200, 203, 217, 227
See application file for complete search history.

(56) References Cited

U.S. PATENT DOCUMENTS

| 8,732,236 B2 | 5/2014 | Altmaier et al. |
| 2007/0044028 A1* | 2/2007 | Dunn ....................... H04N 7/15 715/761 |

(Continued)

FOREIGN PATENT DOCUMENTS

| JP | H10-171967 | 6/1998 |
| JP | 2001-005711 | 1/2001 |

(Continued)

*Primary Examiner* — El Hadji Sall
(74) *Attorney, Agent, or Firm* — Fay Kaplun & Marcin, LLP (57) ABSTRACT A medical support system enables one server bidirectionally connected to one terminal to bidirectionally communicate with another server bidirectionally connected to another terminal. Each of the one server and the other server comprises: a conference processing unit configured to perform a conference between the one terminal and the other terminal; an image sharing processing unit configured to bidirectionally share an image between the one server and the other server; and a control unit configured to control the entire server over a network, wherein the control unit of the one server transmits only operation information sent from the one terminal to the control unit of the other server, and the control unit of the other server controls based on the received operation information.

7 Claims, 9 Drawing Sheets (51) Int. Cl.
*G06F 17/30* (2006.01)
*H04L 29/06* (2006.01)
*G06F 3/0482* (2013.01)
*G06F 3/0484* (2013.01)
*G06Q 50/24* (2012.01)

(56) References Cited

U.S. PATENT DOCUMENTS

2007/0106950 A1* 5/2007 Hutchinson ............ G09B 5/067
 715/761
2008/0030300 A1* 2/2008 Naito ..................... G06Q 30/02
 340/5.1
2012/0079399 A1 3/2012 Ferman et al.
2012/0096091 A1 4/2012 Miyama et al.

FOREIGN PATENT DOCUMENTS

| | | |
|---|---|---|
| JP | 2001-118015 | 4/2001 |
| JP | 2004-062709 | 4/2004 |
| JP | 2005-234633 | 9/2005 |
| JP | 2007-122648 | 5/2007 |
| JP | 2008-217294 | 9/2008 |
| JP | 2009-205278 | 9/2009 |
| JP | 2012-074040 | 4/2012 |
| JP | 2012-084008 | 4/2012 |
| JP | 2013-524632 | 6/2013 |
| WO | 2011/119793 | 9/2011 |

* cited by examiner

MEDICAL SUPPORT SYSTEM AND METHOD THEREOF

PRIORITY CLAIM

This application is a national stage application, filed under 35 U.S.C. §371, of PCT Patent Application Serial No. PCT/JP2012/007898, filed on Nov. 12, 2012, entitled "Medical Assistance System and Method for Same", which is hereby incorporated by reference in its entirety.

BACKGROUND OF THE INVENTION

1. Field of the Invention

The present invention relates to a medical support system and a method thereof. More specifically, the present invention relates to the system that enables a conference through bi-directional sharing of an image using a network, and the method thereof.

2. Description of the Related Art

With a development of communication technology, video conferences can be performed via the network such as the Internet at places that are distant from each other. For example, when the conference is performed in a medical field, the video conference is generally performed using only voice or both voice and the image (video). Also, a medical image is generally transmitted and received over the network and displayed. However, when details of an observation about the image are discussed during the conference, it is difficult to indicate a specific site to the other person without the image even when anatomical terms are used. In addition, when the medical image is transmitted and received, the transmission and reception are generally performed with compressed data, and thus the image may be deteriorated. Furthermore, in a remote place such as a foreign country, it may be necessary to interact with places where band frequency of network lines are different from each other, and the system is also needed to enable the conference even in this case. For example, Japanese Patent Laid-Open No. 2008-217294 discloses a technology that a doctor in a medical facility discusses with a doctor outside of the medical facility using the medical images in real time.

However, Japanese Patent Laid-Open No. 2008-217294 discloses that the real-time discussion is performed using the medical image, but there is no means for indicating a specific site in the image. Therefore, there is a risk that the recognition of the specific site is not properly shared with each other during the discussion. Also, Japanese Patent Laid-Open No. 2008-217294 does not disclose that operation information is transmitted only in one direction without sharing the operation information with each other. When the real-time discussion is performed using the medical image, unless otherwise properly indicated any specific site in the image, it is difficult to recognize the specific site through exchange of only words to thereby make a wrong diagnosis. Therefore, it is preferable to share the specific site recognized with each other and the other operation information with each other. Furthermore, when the conference is performed in remote places, the medical image for conference is compressed and transmitted or received if the band frequency of the network line is narrow, and thus a difference in quality of the shared image may be occurred due to deterioration of the image or the like.

SUMMARY OF THE INVENTION

The present invention provides a medical support system in which a medical image can be shared interacted with each other via a network at distant places in any line situation.

According to an embodiment of the present invention, a medical support system that enables one server bidirectionally connected to one terminal to bidirectionally communicate with another server bidirectionally connected to another terminal is provided, wherein each of the one server and the other server comprises: a conference processing unit configured to perform a conference between the one terminal and the other terminal; an image sharing processing unit configured to bidirectionally share an image between the one server and the other server; and a control unit configured to control the entire server over a network, wherein the control unit of the one server transmits only operation information sent from the one terminal to the control unit of the other server, and the control unit of the other server controls based on the received operation information.

According to the present invention, a medical support system in which a medical image can be shared interacted with each other via a network at distant places in any line situation can be provided.

Further features of the present invention will become apparent from the following description of exemplary embodiments (with reference to the attached drawings).

DESCRIPTION OF THE EMBODIMENTS

A telemedicine network system according to embodiments of the medical support system of the present invention will be described with reference to the drawings. Further, the embodiments shown below are specific preferred examples of the telemedicine network system of the present invention, and although various limitations that are preferable in terms of treatment may be applied, the technical range of the present invention is not limited by these unless specifically described otherwise. Also, components in the embodiment shown below may be appropriately replaced with existing components, and various variations including combinations with other existing components are possible. Therefore, content of the present invention described in the claims is not limited by description of the embodiments shown below.

Figure 1:
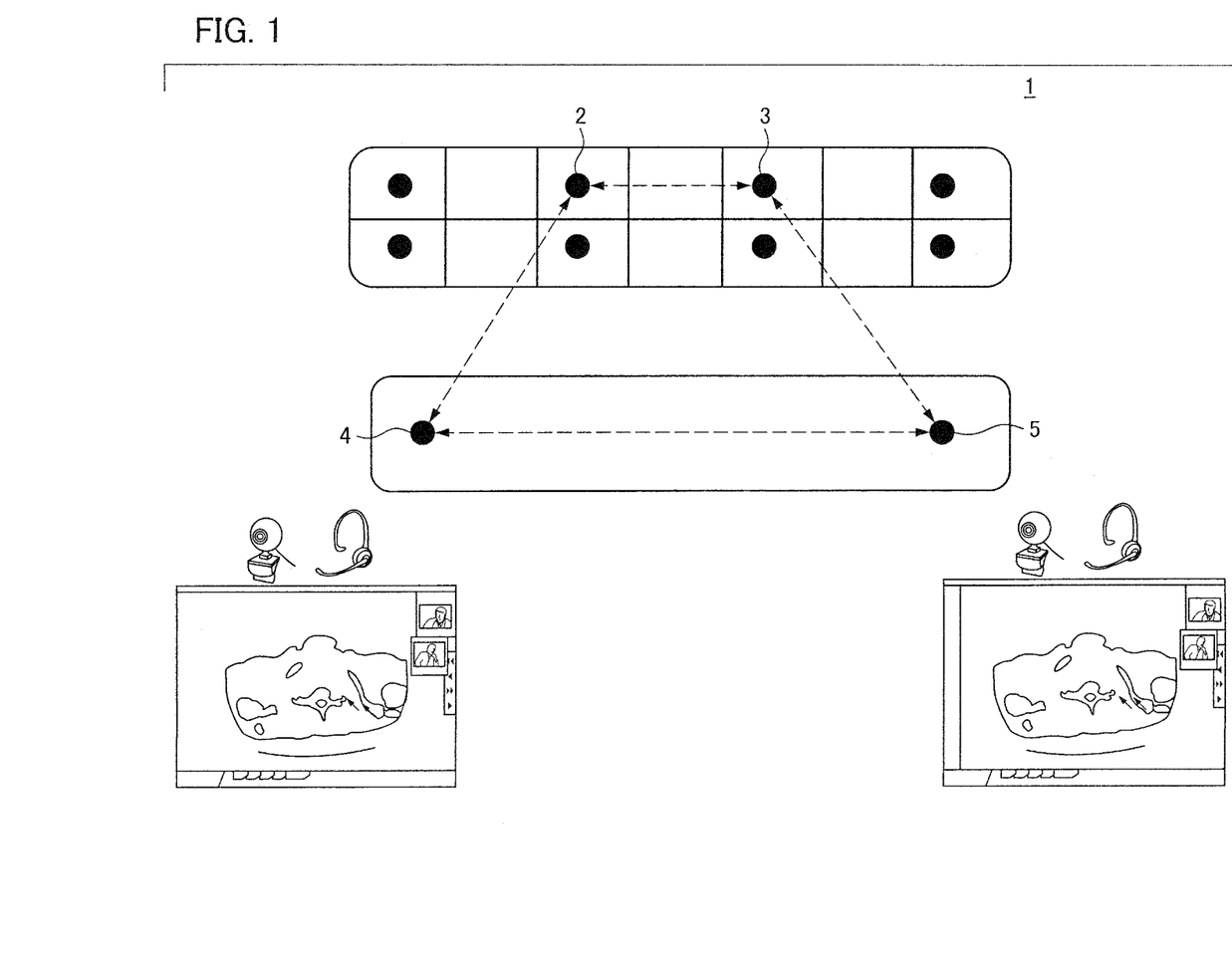
FIG. 1 is a schematic diagram illustrating a conference between two points according to the present invention.

Firstly, with reference to FIG. 1, a telemedicine network system 1 includes a server (one server) 2 and a server (another server) 3 which are connected to each other so as to be able to perform bidirectional communication via the network, and a terminal (one terminal) 4 and a terminal (another terminal) 5 which are bidirectionally connected with the server 2 and the server 3 so as to be able to perform bidirectional communication, respectively. The servers 2 and 3 cause all processing information related to a conference connection, image sharing, or the like according to the present invention to be bidirectionally shared. The terminals 4 and 5 may be general-purpose devices connected to the network comprising a device capable of displaying a medical image, a video device such as a web camera through which the conference can be performed, and an audio device such as a microphone. For example, the terminals 4 and 5 may be portable terminals such as a small PC, a portable telephone or a smartphone, or stationary devices such as a desktop PC. Here, in the present embodiment, the conference may be a conference that is performed by a plurality of (two or more) terminals and performed by transmitting a video and voice with each other. However, the conference may be performed with only the voice without the image. In addition, the medical image is a 2D (two-dimensional) or 3D (three-dimensional) image used in the medical field, such as an MRI image or a CT image, but the medical image is not limited thereto and may be, for example, an image such as a JPEG or GIF that is generally widely used. Note that the telemedicine network system 1 is provided by so-called cloud computing. Here, the cloud computing refers to a form of providing computing resources such as the servers 2 and 3 to an external user over the network with software, hardware, processing performance, a storage area, a file, data, or the like.

Figure 2:
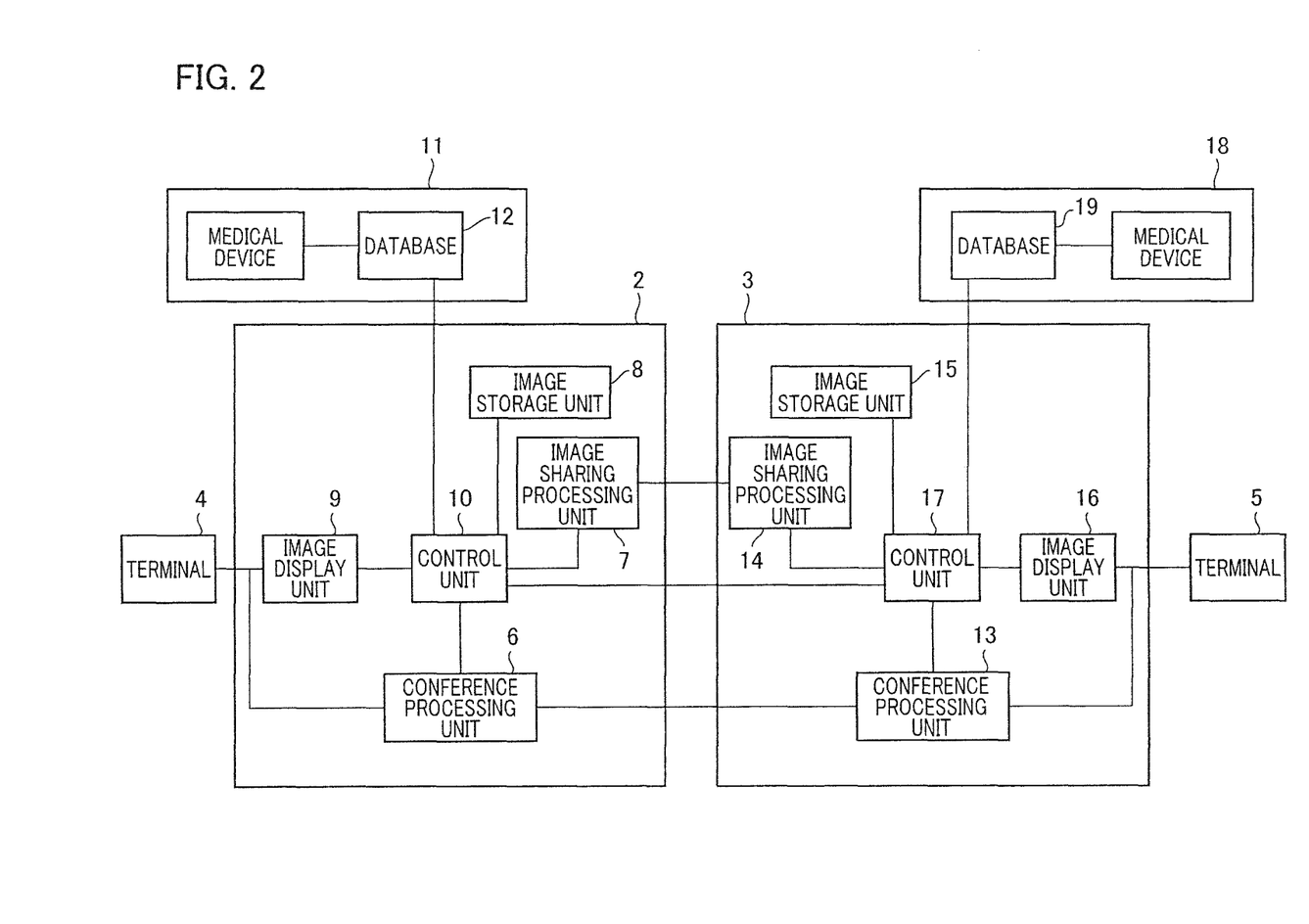
FIG. 2 is a block diagram illustrating a server according to an embodiment of the present invention.

With reference to FIG. 2, the servers 2 and 3 comprise conference processing units 6 and 13, image sharing processing units 7 and 14, image storage units 8 and 15, image display units 9 and 16, and control units 10 and 17, respectively. The conference processing units 6 and 13 perform start processing of the conference based on operation information for the conference start from the terminals 4 and 5. The image sharing processing units 7 and 14 perform processing for sharing the medical image required for the conference. The image storage units 8 and 15 temporarily (only during the conference) store the medical image required for the conference which is shared by image sharing processing units 7 and 14. The image display units 9 and 16 send display information such as the shared medical image and the video during the conference to the terminals 4 and 5 so that the display information is displayed on the terminals 4 and 5. The control units 10 and 17 control the entire servers thereof, and are connected to a database that is connected to a medical device or the like at a medical facility such as a hospital and stores the medical image, respectively.

Figure 3:
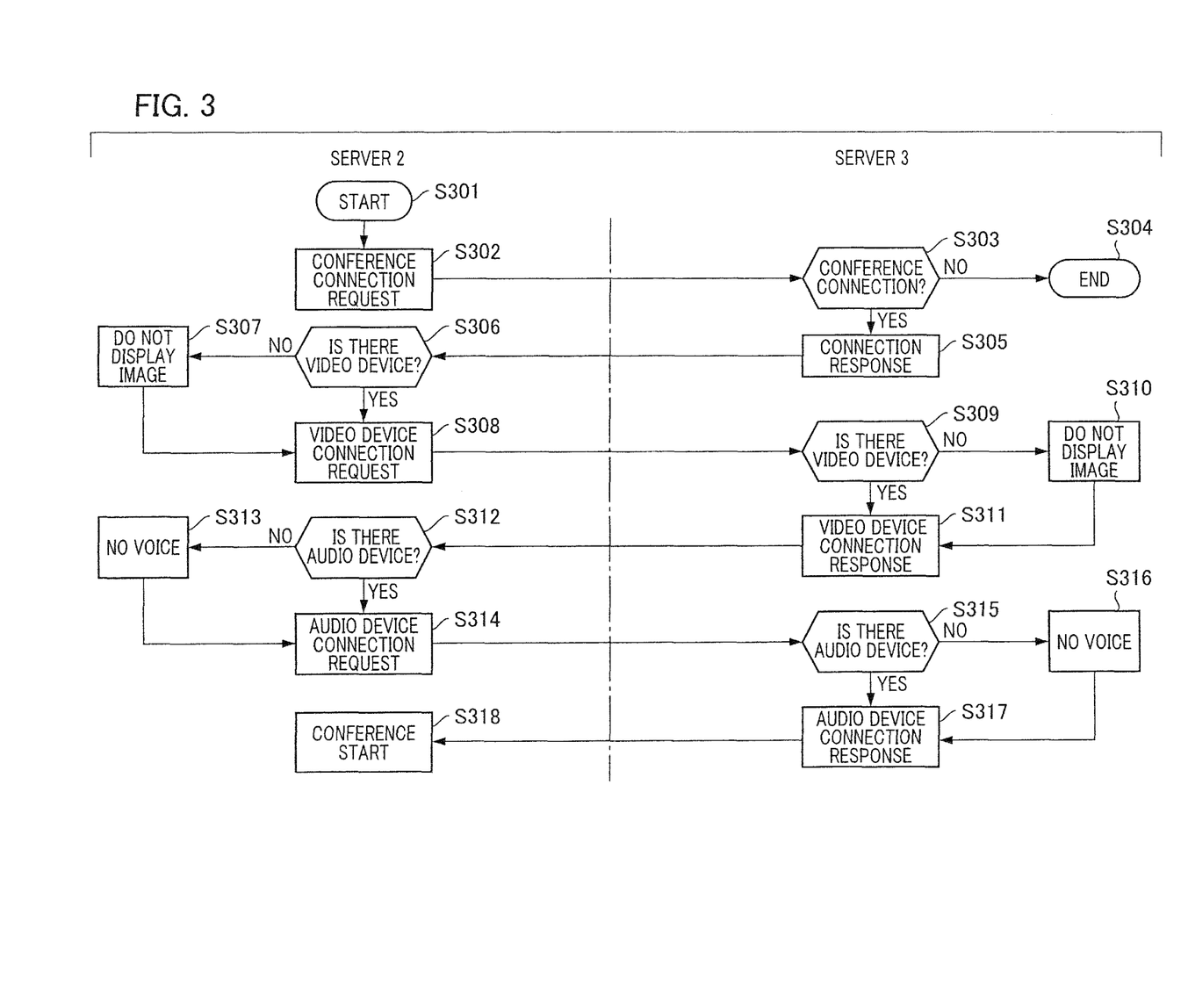
FIG. 3 is a flowchart illustrating a conference processing according to an embodiment the present invention.

Next, a flow of the conference processing when the conference is started from the terminal 4 to the terminal 5 will be described with reference to FIG. 3. Firstly, the operation information for the start of the conference processing is transmitted from the terminal 4 to the control unit 10 of the server 2, and the control unit 10 of the server 2 causes the conference processing unit 6 of the server 2 to start the conference processing. In step S301, the conference processing unit 6 starts the conference. Then, in step S302, a conference request is transmitted from the conference processing unit 6 of the server 2 to the conference processing unit 13 of the server 3. In step S303, the conference processing unit 13 of the server 3 that has received the conference request determines whether or not the connection for the conference can be performed. When the conference is not performed (N), the processing proceeds to step S304 and ends. When the conference is performed (Y), the processing proceeds to step S305 and the response of the connection is transmitted to the conference processing unit 6 of the server 2.

Next, in step S306, the conference processing unit 6 of the server 2 determines whether or not there is the video device such as the web camera to be used during the conference. When there is no video device (N), the processing proceeds to step S307, and the conference is performed without displaying the video. When there is the video device (Y), the processing proceeds to step S308. Then, in step S308, the connection request for the video device is transmitted to the conference processing unit 13 of the server 3. In step S309, the conference processing unit 13 of the server 3 that has received the connection request for the video device determines whether or not there is the video device. When there is no video device (N), the processing proceeds to step S310 and the conference is performed without displaying the video. When there is the video device (Y), the processing proceeds to step S311. Then, step S311, the response of the video device connection is transmitted to the conference processing unit 6 of the server 2.

Next, in step 312, the conference processing unit 6 of the server 2 determines whether or not there is an audio device. When there is no audio device (N), the processing proceeds to step S313 and the conference is performed without outputting voice. When there is the audio device (Y), the processing proceeds to step S314 and the connection request for the audio device is transmitted to the conference processing unit 13 of the server 3. In step S315, the conference processing unit 13 of the server 3 that has received the connection request for the audio device determines whether or not there is the audio device. When there is no audio device (N), the processing proceeds to step S316 and the conference is performed without outputting voice. When there is the audio device (Y), the processing proceeds to step S317. Then, in step S317, the response of the connection for the audio device is transmitted to the conference processing unit 6 of the server 2. After the connection processing for the video device and the audio device is completed, in step S318, the conference is started. Note that, while the conference processing from the terminal 4 to the terminal 5 has been described in the present embodiment, the conference may be started from the terminal 5 to the terminal 4. In this case, the flow is opposite to the flow of the conference processing described the above. In addition, the flow is not limited thereto and may be executed in a different order or the flows may be executed at the same time.

Figure 4:
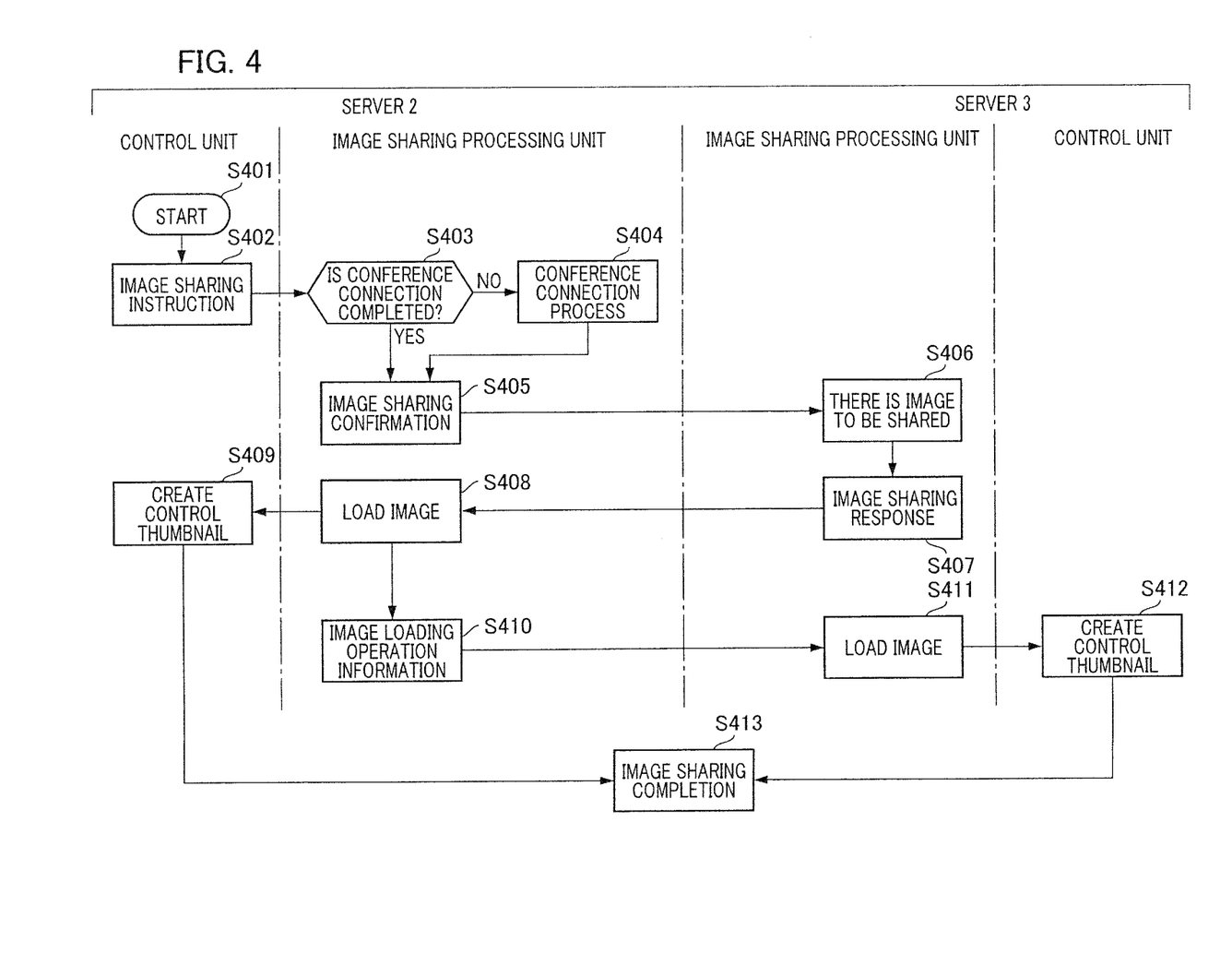
FIG. 4 is a flowchart illustrating an image sharing processing when there is a shared image.
Figure 5:
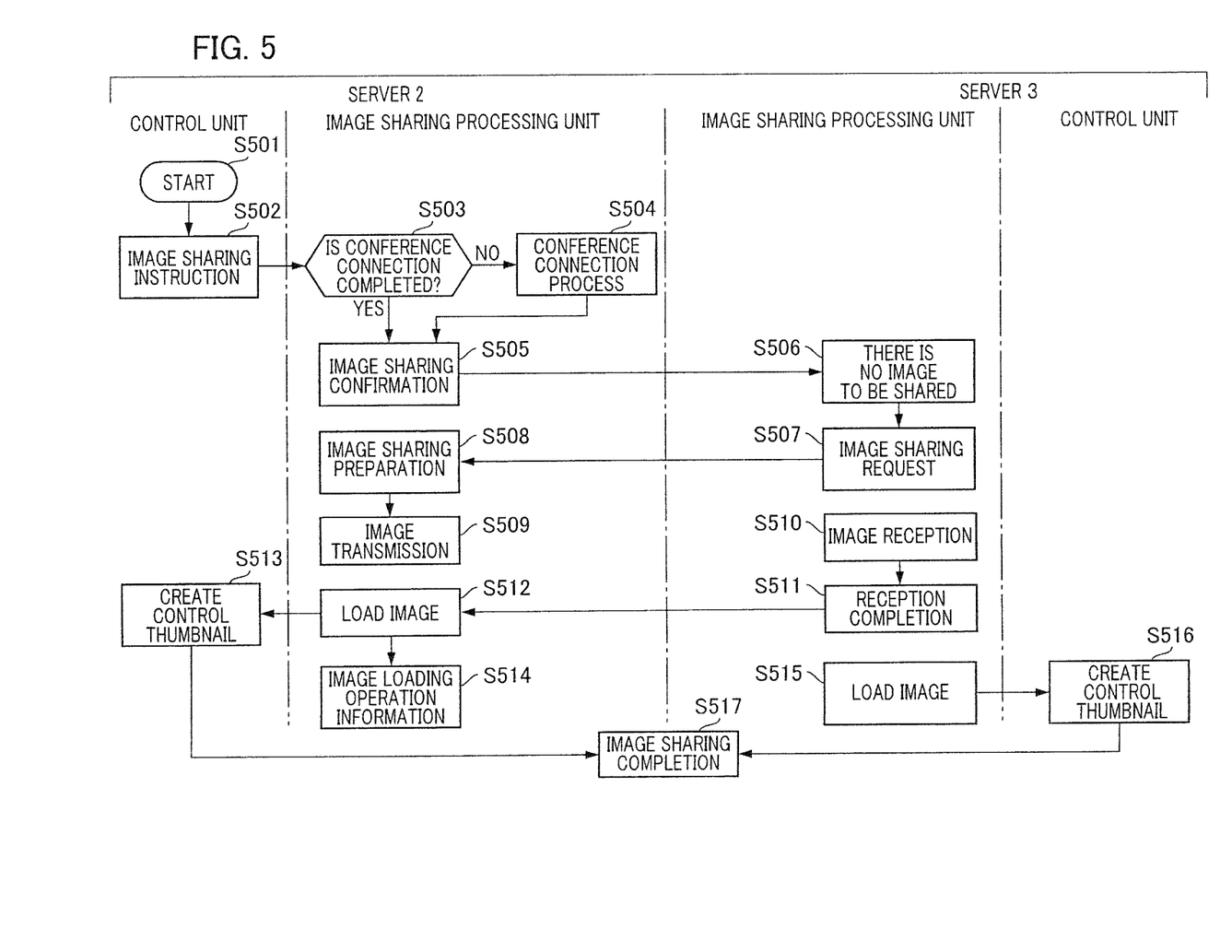
FIG. 5 is a flowchart illustrating an image sharing processing when there is no shared image.

Next, the flow of the image sharing processing will be described with reference to FIGS. 4 and 5. Firstly, the flow in which the medical image to be shared during the conference is held in both of the servers 2 and 3 will be described with reference to FIG. 4. In step S401, the control unit 10 of the server 2 starts image sharing. In step S402, the control unit 10 transmits an instruction for sharing the medical image to be shared during the conference to the image sharing processing unit 7 of the server 2. Next, in step S403, the image sharing processing unit 7 determines whether or not the conference processing is completed. When the conference processing is not completed (N), the processing proceeds to step S404 and the conference processing is performed as described the above. When the conference processing is completed (Y), the processing proceeds to step S405. Then, in step S405, the image sharing processing unit 7 transmits confirmation whether or not there is the medical image to be shared during the conference to the image sharing processing unit 14 of the server 3. In step S406, when there is the medical image to be shared, the processing proceeds to step S407. Then, in step S407, the response of the image sharing response is transmitted to the image sharing processing unit 7 of the server 2. A case in which there is no medical image to be shared will be described below with reference to FIG. 5.

Next, in step S408, the image sharing processing unit 7 of the server 2 loads the medical image to be shared and temporarily stores the medical image in the image storage unit 8. When the medical image is temporarily stored in the image storage unit 8 of the server 2, in step S409, the control unit 10 of the server 2 creates a control thumbnail of the medical image to be shared. After or simultaneously with the processing in step S409, in step S410, the operation information for loading the image is transmitted to the image sharing processing unit 14 of the server 3. In step S411, the image sharing processing unit 14 of the server 3 receives the operation information transmitted from the image sharing processing unit 7 of the server 2, loads the medical image to be shared, and temporarily stores the medical image in the image storage unit 15 of the server 3. When the medical image is temporarily stored in the image storage unit 15, in step S412, the control unit 17 of the server 3 creates the control thumbnail. The sharing processing of the medical image required during the conference is completed with completion of the control thumbnail creation in the server 2 and the server 3 (step S413), and the respective servers hold the same medical image.

Next, a flow in which one of the servers does not have the medical image necessary to be shared in the conference will be described with reference to FIG. 5. Since the processing in steps S501 to S505 are the same as in steps S401 to S405 described above, detailed description thereof will be omitted. Next, in step S506, since there is no medical image to be shared, the processing proceeds to step S507 and the image sharing processing unit 14 of the server 3 transmits the request for the medical image to be shared to the image sharing processing unit 7 of the server 2. In step S508, the image sharing processing unit 7 of the server 2 that receives the request for the medical image to be shared prepares the medical image to be shared for transmitting. At this time, the image sharing processing unit 7 of the server 2 prepares the medical image for transmitting that is not subjected to processing such as compression processing or the like in the database 12 in the medical facility via the control unit 10. After completing the preparation for the image to be shared, in step 509, the image sharing processing unit 7 of the server 2 transmits the medical image to the image sharing processing unit 14 of the server 3. At this time, the image sharing processing unit 7 of the server 2 transmits the medical image without being subjected to a processing such as the compression processing or the like. In step S510, the image sharing processing unit 14 of the server 3 receives the medical image, and, in step S511, the image sharing processing unit 14 of the server 3 transmits reception completion of the medical image to be shared to the image sharing processing unit 7 of the server 2.

Since the processing in steps S512 to S517 are the same as in steps S408 to S413 described above, detailed description thereof will be omitted. Note that, while the image sharing processing is performed from the server 2 to the server 3 in the present embodiment, the image sharing processing may be performed from the server 3 to the server 2. In this case, the flow is opposite to the flow of the image sharing processing as described the above. In addition, the flow is not limited thereto and may be executed in the different order or the flows may be executed at the same time. The shared medical image is displayed on the respective terminals 4 and 5 through the image display units 9 and 16. At this time, the shared medical image is not subjected to processing such as the compression processing or the like, and thus, when both the terminals 4 and 5 use the same display unit, fidelity of the medical image displayed on the terminal 4 is the same as the fidelity of the medical image displayed on the terminal 5.

In the present embodiment, the flow that the image sharing processing is performed after the conference processing has been described, but the present invention is not limited thereto and the processing may be independently executed at the same time or the conference processing may be executed after the image sharing processing. The conference processing is independently from the image sharing processing at the same time to thereby be able to shorten the time from start of the connection by the terminals between those who perform the conference to start of the actual conference.

Figure 6:
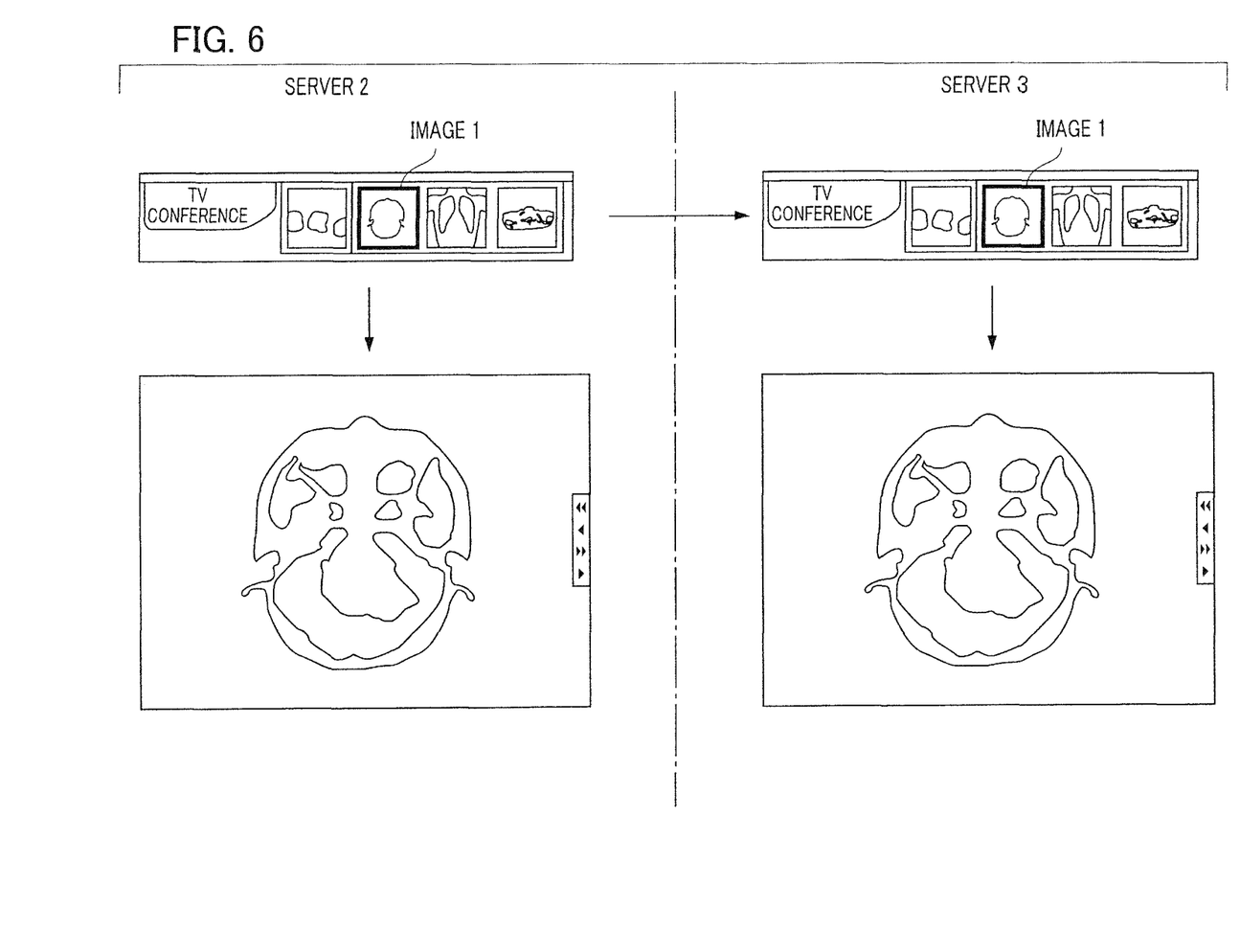
FIG. 6 is a schematic diagram illustrating image selection according to an embodiment of the present invention.
Figure 7:
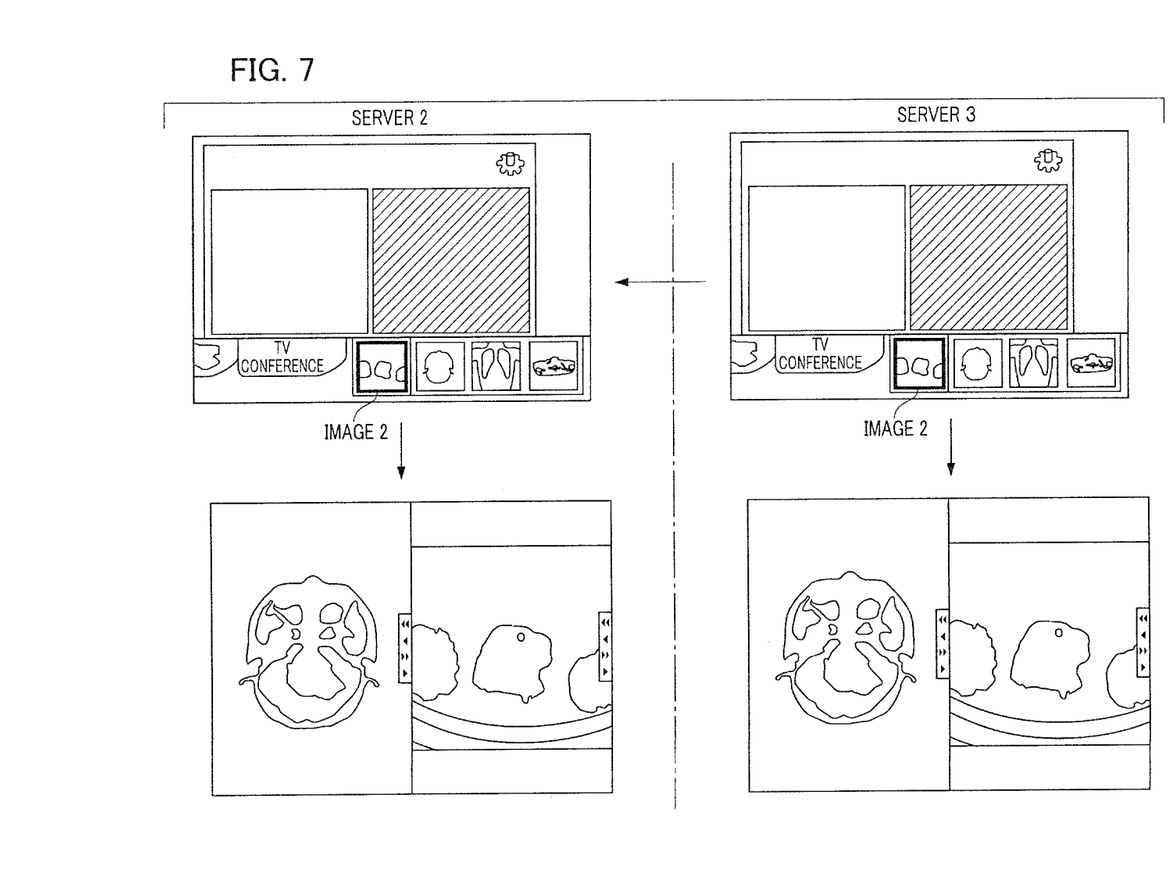
FIG. 7 is a schematic diagram illustrating 2-screen selection according to an embodiment of the present invention.
Figure 8:
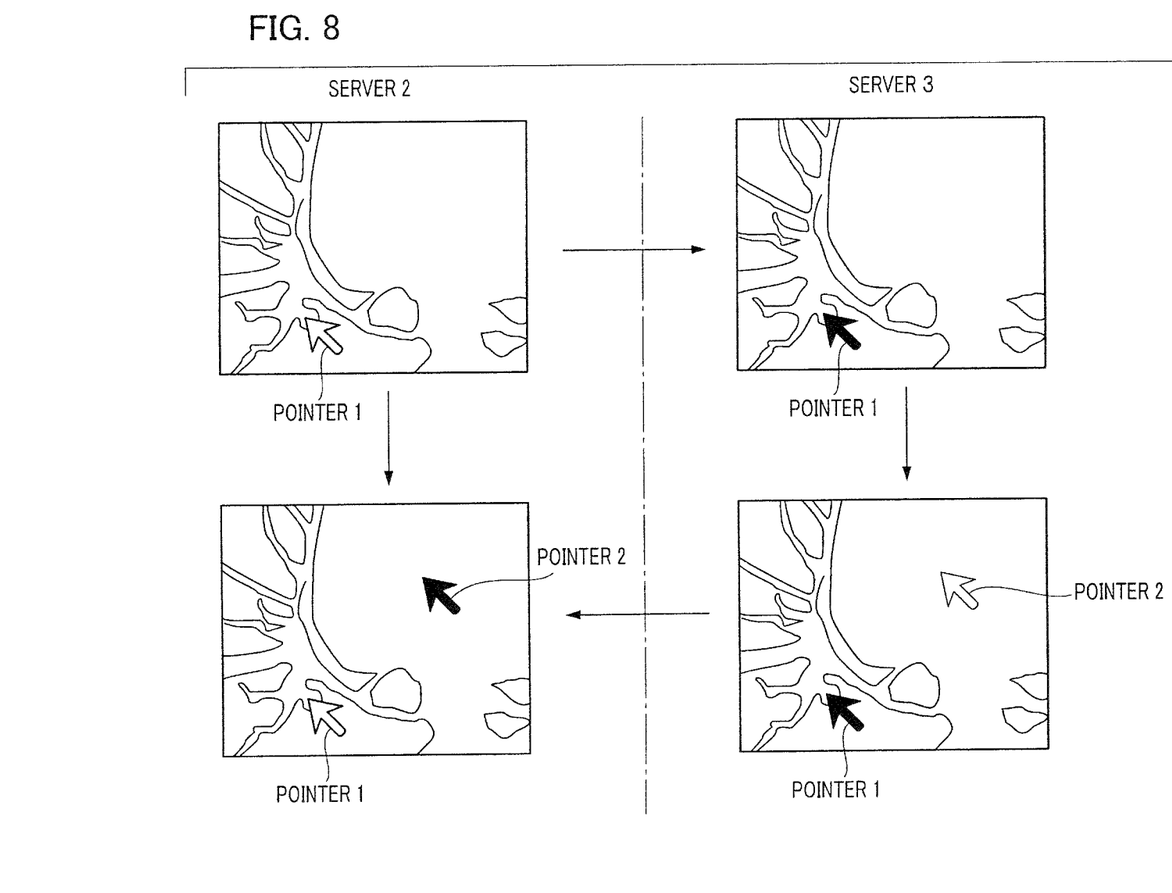
FIG. 8 is a schematic diagram illustrating pointer display according to an embodiment of the present invention.

Next, an operation of the medical image to be shared during the conference and a method for sharing information regarding the operation will be described with reference to FIGS. 6 to 8. Firstly, the method for sharing the operation information when an image 1 is selected among thumbnail images displayed on the terminal 4 will be described with reference to FIG. 6. Firstly, the operation for selecting the image 1 among the thumbnail images is performed on the terminal 4. Next, operation information for selecting the image 1 among the thumbnail images is transmitted from the terminal 4 to the server 2. The control unit 10 of the server 2 causes the image display unit 9 of the server 2 to display the image 1 (the medical image) selected among the thumbnail images based on the transmitted operation information. Then, the image display unit 9 transmits the display information to the terminal 4, and the selected image 1 is displayed on a screen of the terminal 4. After or simultaneously causing the image display unit 9 to display image 1, the control unit 10 of the server 2 transmits the operation information to the control unit 17 of the server 3. The control unit 17 of the server 3 selects the image 1 among the thumbnail images based on the received operation information and causes the image display unit 16 of the server 3 to display the image 1. Then, the image display unit 16 transmits the display information to the terminal 5, and the selected image 1 is displayed on the screen of the terminal 5.

Next, the method for sharing the operation information when the plurality of images are displayed will be described with reference to FIG. 7. In other words, the method for sharing the operation information when image 2 and image 1 are displayed side by side among the thumbnail images displayed on the terminal 5 will be described with reference to FIG. 7. Firstly, the operation of selecting the image 2 among the thumbnail images in addition to the image 1 displayed on the terminal 5 and selecting an image layout for displaying the image 2 is performed. Next, the operation information of the operation performed on the terminal 5 is transmitted from the terminal 5 to the control unit 17 of the server 3. At this time, as shown in FIG. 7, the image layout for displaying the image 1 and the image is selected. The control unit 17 causes the image display unit 16 of the server 3 to display the two medical images side by side based on the operation information sent from the terminal 5, the image display unit 16 transmits the display information to the terminal 5, and the selected images 1 and 2 are displayed on the screen of the terminal 5 based on the selected image layout. After or simultaneously causing the image display unit 16 to display the images based on the operation information of the terminal 5, the control unit 17 of the server 3 transmits the operation information to the control unit 10 of the server 2. The control unit 10 of the server 2 selects the image 2 among the thumbnail images based on the received operation information, and causes the image display unit 9 of the server 2 to display the two medical images side by side according to the image layout. Then, the image display unit 9 transmits the display information to the terminal 4, and the image 1 and the image 2 are displayed on the screen of the terminal 4 according to the selected layout. While the method of displaying the two medical images side by side has been described in the present embodiment, the present invention is not limited thereto, and the present invention may be similarly embodied using the method of operating the images of each other based on the operation information of each other, even when two or more images are caused to be displayed side by side.

Next, the method for sharing the operation information when pointers of each other are caused to be displayed in the terminals 4 and 5, respectively will be described with reference to FIG. 8. Firstly, the operation of displaying the pointer 1 operated on the terminal 4 is performed, and the terminal 4 transmits the operation information to the control unit 10 of the server 2. The control unit 10 of the server 2 causes the image display unit 9 of the server 2 to display the pointer 1, the image display unit 9 transmits the display information to the terminal 4, and the pointer 1 operable on the terminal 4 is displayed on the screen of the terminal 4. After or simultaneously causing the image display unit 9 to display the pointer 1, the control unit 10 of the server 2 transmits the operation information to the control unit 17 of the server 3. The control unit 17 of the server 3 causes the image display unit 16 of the server 3 to display the pointer 1 based on the received operation information, the image display unit 16 transmits the display information to the terminal 5, and the pointer 1 that is not operable on the terminal 5 is displayed on the screen of the terminal 5.

Next, after or simultaneously displaying the pointer 1, the control unit 17 of the server 3 causes the image display unit 16 to display the pointer 2 operable on the terminal 5, the image display unit 16 transmits the display information to the terminal 5, and the pointer 2 operable on the terminal 5 is displayed on the screen of the terminal 5 in addition to the pointer 1. After or simultaneously causing the image display unit 16 to display the pointer 2, the control unit 17 of the server 3 transmits the operation information for displaying the pointer 2 to the control unit 10 of the server 2. The control unit 10 of the server 2 causes the image display unit 9 of the server 2 to display the pointer 2 based on the received operation information, the image display unit 9 transmits the operation information to the terminal 4, and the pointer 2 that is not operable on the terminal 4 is displayed on the screen of the terminal 4 in addition to the pointer 1.

In this case, colors of the pointer 1 and the pointer 2 displayed on the screen are changed so that the pointer 1 and the pointer 2 are distinguished from each other. For example, on the screen of the terminal 4, the pointer 1 operable on the terminal 4 is displayed in white, and the pointer 2 that is not operable on the terminal 4 is displayed in black. In contrast, on the screen of the terminal 5, the pointer 2 operable on the terminal 5 is displayed in white, and the pointer 1 that is not operable on the terminal 4 is displayed in black. After both pointers are displayed, the pointer 1 or the pointer 2 is moved based on the operation information sent from the terminal 4 or the terminal 5. For example, firstly, when the operation of laterally moving the pointer 1 operable on the terminal 4 is performed, the terminal 4 sends operation information to the control unit 10 of the server 2. The control unit 10 of the server 2 causes the image display unit 9 of the server 2 to display the pointer 1 moving based on the operation information, the image display unit 9 sends the display information to the terminal 4, and the pointer 1 is displayed so as to laterally move according to the operation on the terminal 4. After or simultaneously causing the image display unit 9 to display the pointer 1, the control unit 10 of the server 2 sends the operation information of the pointer 1 to the control unit 17 of the server 3. The control unit 17 of the server 3 causes the image display unit 16 of the server 3 to display the pointer 1 moving laterally based on the received operation information, the image display unit 16 sends the display information to the terminal 5, and the pointer 1 is displayed is displayed so as to laterally move on the terminal 5. In the present embodiment, while the colors of the pointers are white and black, the present invention is not limited thereto, and the colors of the pointers displayed on the screen of each terminal may be any colors as long as the operable pointer and the other pointer(s) (that is (are) not operable) can be distinguished from each other.

The operation of the medical image to be shared and the method of sharing the information for the operation during the conference have been described above. However, the present invention is not limited to this method, and the information for the operation performed by the terminal 4 or the terminal 5 may be shared over the network, and the operation may be performed based on the operation information and displayed on terminals of each other. Further, the operation of the medical image is not limited to the present embodiment, and may include, for example, at least one of various functions of a workstation according to the medical image, such as luminance/contrast adjustment display, zoom-in and zoom-out display, panning, partial zoom-in display, window frame fitting display, pixel equal-magnification display, full scale display, black and white highlight display, a color palette, an RGB component, an HSV component, an LUT, smoothing, sensitization, edge detection, a median filter, a threshold value, display condition preset, horizontal rotation display, vertical highlight display, horizontal highlight display, synchronized display of images in the same series, synchronized display of images in a plurality of series, angle measurement, measurement of angle relative to a reference line, length measurement, CT value measurement, oval ROI measurement, polygonal ROI measurement, arbitrary region ROI measurement, graphic drawing, text drawing, histogram display, marking, cardiothoracic ratio measurement, drawing overlay removal, image information display, overlay display/non-display, display layout setting, tile mode display, stack mode display, multiple series display, multiple series synchronized display, thumbnail image display, scout image display, reference line display, cine display, video display, series mode display, study mode display, hanging protocol function, display of mammography images in horizontal alignment, mammography image breast position automatic alignment, a mammography image horizontal interlocking magnifying glass, shaping measurement including any one of a cobb angle, FTA, and a sharp angle, implant simulation, an expansion correction function, or in the case of a 3D image a function of volume rendering, a 3D cursor, MPR, CPR, MIP, MinIP, Curved MPR, oblique, fusion, inter-volume calculation, a virtual endoscope, volume or distance measurement, fat measurement, extraction, composition, editing, or analysis. Also in this case, the operation information may be mutually shared with each other, and the same image or the like may be displayed between the terminals. Note that, after ending of the conference, the images temporarily stored in the image storage units 8 and 15 may be remained to be stored or may be erased.

Furthermore, in the present embodiment, the conference processing, the image sharing processing, and the operation of the shared image at the time of the conference between the terminal 4 and the terminal 5 via the servers 2 and 3 have been described. However, the present embodiment may be applied between the servers without using the terminal 4 and the terminal 5, for example, as long as each of the servers 2 and 3 includes the video device such as the web camera through which the conference is possible, the audio device such as the microphone, and the monitor or the display that displays the image to be shared.

Figure 9:
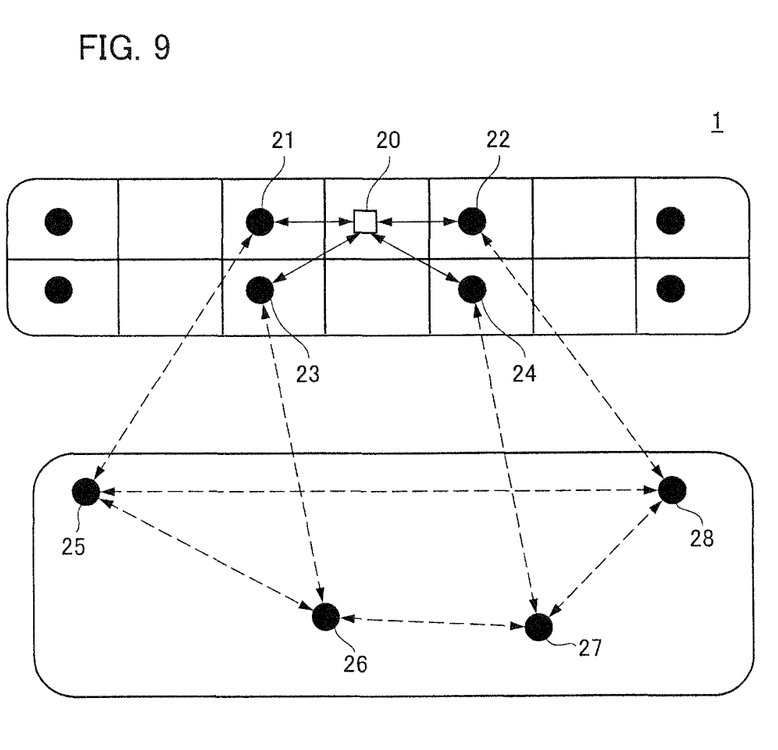
FIG. 9 is a schematic diagram illustrating a conference among a plurality of terminals according to the present invention.

Next, a flow in which the conference is performed among a plurality of (three or more) terminals will be described with reference to FIG. 9. When the conference and the sharing of the medical image are performed in three or more terminals, the conference and the sharing are performed via a multi-connection unit that is connected to respective servers and enables bidirectional communication. In this case, for example, when the conference processing and the image sharing processing are performed from a terminal 25, all of the processing as described the above are simultaneously executed at the plurality of terminals. Furthermore, the operation information for the medical image is shared among all the servers via the multi-connection unit, and the same image or the like is displayed on the respective terminals. In this case, the pointer may be displayed in any color as long as the operable pointer and the other pointers can be distinguished, and the number of colors is not limited.

According to the present embodiment, the image such as the medical image can be displayed and operated during the conference performed by transmitting the video and/or the voice with each other. Therefore, it is possible to provide a medical support system in which a medical image can be mutually shared over a network at distant places in any line situation and can be bidirectionally exchanged by mutual sharing of operation information.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

What is claimed is:

1. A medical support system that enables one server bidirectionally connected to one terminal to bidirectionally communicate with another server bidirectionally connected to another terminal via a network, wherein each of the one server and the other server comprises:
    a conference processing unit configured to perform a conference which is performed by transmitting a video and voice or only the voice with each other between the one terminal and the other terminal;
    an image sharing processing unit configured to bidirectionally share a medical image, which is different from the video and is stored in a database in a medical facility, between the one server and the other server;
    an image storage unit configured to temporarily store a shared image shared by the image sharing processing unit;
    a control unit configured to control own server based on operation information transmitted from the one terminal or the other terminal; and
    an image displaying unit configured to transmit display information for displaying the shared image of which the display is controlled by the control unit on the one terminal or the other terminal to the one terminal or the other terminal,
    wherein the one terminal or the other terminal displays the shared image based on the display information transmitted from the one image displaying unit or the other image displaying unit, and transmits the operation information to the control unit of the server,
    wherein the control unit of the one server or the other server creates a thumbnail image of the shared image, respectively, when the sharing of the shared image is completed and the shared image is stored in the one image storage unit and the other image storage unit,
    wherein, in the one server, the control unit selects the thumbnail image among the created thumbnail image based on the operation information transmitted from the one terminal and transmits the operation information to the control unit of the other server, the image display unit transmits the display information for displaying the selected thumbnail image on the one terminal to the one terminal, and
    wherein, in the other server, the control unit selects the thumbnail image which is the same as that has been selected by the control unit of the one server among the created thumbnail image based on the operation information transmitted from the one server, and the image display unit transmits the display information for displaying the selected thumbnail image on the other terminal.

2. The medical support system according to claim 1, wherein the control unit causes the conference processing unit and the image sharing processing unit to be independently executed at the same time.

3. The medical support system according to claim 1, wherein, when there is no shared image in the image storage unit of the other server, the image sharing processing unit of the one server transmits the image to be shared from the database in the medical facility connected to the one server to the image sharing processing unit of the other server, and the image to be shared is stored in the image storage unit.

4. The medical support system according to claim 1, wherein each the image storage unit erases or remains to store the image to be shared that has been stored in the image storage unit.

5. The medical support system according to claim 1, wherein the conference is executed between a plurality of two or more terminals.

6. The medical support system according to claim 1, wherein display and an operation of the image to be shared are simultaneously performed during the conference.

7. The medical support system according to claim 1, wherein the image to be shared is a medical image that is not subjected to a compression processing.

* * * * *